United States Patent
Eggers et al.

(10) Patent No.: US 9,766,313 B2
(45) Date of Patent: Sep. 19, 2017

(54) MR IMAGING USING APT CONTRAST ENHANCEMENT AND SAMPLING AT MULTIPLE ECHO TIMES

(71) Applicant: KONINKLIJKE PHILIPS N.V., Eindhoven (NL)

(72) Inventors: Holger Eggers, Eindhoven (NL); Jochen Keupp, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 252 days.

(21) Appl. No.: 14/387,421

(22) PCT Filed: Mar. 21, 2013

(86) PCT No.: PCT/IB2013/052244
§ 371 (c)(1),
(2) Date: Sep. 23, 2014

(87) PCT Pub. No.: WO2013/150407
PCT Pub. Date: Oct. 10, 2013

(65) Prior Publication Data
US 2015/0051474 A1 Feb. 19, 2015

Related U.S. Application Data

(60) Provisional application No. 61/619,601, filed on Apr. 3, 2012.

(30) Foreign Application Priority Data

Apr. 3, 2012 (EP) .................................. 12162970

(51) Int. Cl.
*G01R 33/48* (2006.01)
*G01R 33/56* (2006.01)
(Continued)

(52) U.S. Cl.
CPC ..... *G01R 33/4828* (2013.01); *G01R 33/5605* (2013.01); *A61B 5/055* (2013.01); *G01R 33/243* (2013.01); *G01R 33/5617* (2013.01)

(58) Field of Classification Search
CPC .. A61B 5/055; G01R 33/243; G01R 33/4828; G01R 33/5605; G01R 33/5617
See application file for complete search history.

(56) References Cited

U.S. PATENT DOCUMENTS 6,962,769 B2   11/2005  Shao
2011/0288402 A1*  11/2011  Pikkemaat ......... G01R 33/5616
                                              600/420
(Continued)

FOREIGN PATENT DOCUMENTS

WO   WO 2010/073184   *   7/2010

OTHER PUBLICATIONS

Song et al., "CEST phase mapping using a Length and Offset VARied Saturation (LOVARS) scheme", Magn Reson Med., vol. 68, Issue 4, published online Jan. 2012, pp. 1074-1086.*

(Continued)

*Primary Examiner* — Katherine Fernandez (57) ABSTRACT

The invention relates to a method of CEST or APT MR imaging of at least a portion of a body (10) placed in a main magnetic field $B_0$ within the examination volume of a MR device. The method of the invention comprises the following steps: •a) subjecting the portion of the body (10) to a saturation RF pulse at a saturation frequency offset; •b) subjecting the portion of the body (10) to an imaging sequence comprising at least one excitation/refocusing RF pulse and switched magnetic field gradients, whereby MR signals are acquired from the portion of the body (10) as spin echo signals; •c) repeating steps a) and b) two or more times, wherein the saturation frequency offset and/or a echo time shift in the imaging sequence are varied, such that a different (Continued)

combination of saturation frequency offset and echo time shift is applied in two or more of the repetitions; •d) reconstructing a MR image and/or $B_0$ field homogeneity corrected APT/CEST images from the acquired MR signals. Moreover, the invention relates to a MR device (1) for carrying out the method of the invention and to a computer program to be run on a MR device.

13 Claims, 3 Drawing Sheets

(51) Int. Cl.
*G01R 33/24* (2006.01)
*G01R 33/561* (2006.01)
*A61B 5/055* (2006.01)

(56) References Cited

U.S. PATENT DOCUMENTS

2012/0019245 A1* 1/2012 Reddy ............... G01R 33/5601
 324/309
2012/0025823 A1 2/2012 Jellus

OTHER PUBLICATIONS

Ragan et al., "A 2-point Dixon Technique Provides Robust Fat Suppression for Multi-mouse Imaging", J Magn Reson Imaging, vol. 31, Issue 2, Feb. 2010, pp. 510-514.*

Zhou, et al "Practical Data Acquisition Method for Human Brain Tumor Amide Proton Transfer (APT) Imaging", Magnetic Resonance in Medicine, vol. 60, 2008, pp. 842-849.
Keupp, J. et al "CEST-Dixon MRI for Sensitive and Accurate Measurement of Amide-Proton Transfer in Human 3T", Proc. Int'l Society for Magnetic Resonance in Medicine, 2010, pp. 1520.
Zhou, J. et al "Chemical Exchange Saturation Transfer Imaging and Spectroscopy", Progress in Nuclear Magnetic Resonance Spectroscopy, vol. 48, No. 2-3, May 2006, pp. 109-136.
Wei, W. et al "Improving Amide Proton Transfer Imaging with Dual Echo B0 Mapping for Field Inhomogeneity Correction at 3T", Proc. Int'l Society for Magnetic Resonance in Medicine, 2010, pp. 2986.
Sun, Phillip Zhe et al "Suppression of Lipid Artifacts in Amide Proton Transfer Imaging" Magnetic Resonance in Medicine, vol. 54, No. 1, Jan. 2005, pp. 222-225.
Zhu, He et al "Fast 3D Chemical Exchange Saturation Transfer (CEST) Imaging of the Human Brain", Magnetic Resonance in Medicine, vol. 64, No. 3, Sep. 2010, pp. 638-644.
Jones, Craig K. et al "Amide Proton Transfer Imaging of Human Brain Tumors at 3T", Magnetic Resonance in Medicine, Vo. 56, 2006, pp. 585-592.
Zhou, Jinyuan et al "Using the Amide Proton Signals of Intracelular Proteins and Peptides to Detect pH Effects in MRI", Nature Medicine Technical Reports, vol. 9, No. 8, 2003.
Zhou, Jinyuan et al "Differentiation between Glioma and Radiation Necrosis using Molecular Magnetic Resonance Imaging of Endogenous Proteins and Peptides", Nature Medicine Technical Reports,vol. 17, No. 1, Jan. 2011.

* cited by examiner

MR IMAGING USING APT CONTRAST ENHANCEMENT AND SAMPLING AT MULTIPLE ECHO TIMES

CROSS-REFERENCE TO PRIOR APPLICATIONS

This application is the U.S. National Phase application under 35 U.S.C. §371 of International Application No. PCT/IB2013/052244, filed on Mar. 21, 2013, which claims the benefit of U.S. Provisional Patent Application No. 61/619,601, filed on Apr. 3, 2012 and European Patent Application No. 12162970.3, filed on Apr. 3, 2012. These applications are hereby incorporated by reference herein.

FIELD OF THE INVENTION

The invention relates to the field of magnetic resonance (MR) imaging. It concerns a method of MR imaging of at least a portion of a body placed in a main magnetic field $B_0$ within the examination volume of a MR device. The invention also relates to a MR device and to a computer program for a MR device.

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

BACKGROUND OF THE INVENTION

According to the MR method in general, the body of the patient to be examined is arranged in a strong, uniform magnetic field $B_0$ whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse) while the magnetic field of the RF pulse extends perpendicular to the z-axis, so that the magnetization performs a precession about the z-axis. This motion of the magnetization describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°). The RF pulse is radiated toward the body of the patient via a RF coil arrangement of the MR device. The RF coil arrangement typically surrounds the examination volume in which the body of the patient is placed.

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within the examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils. Alternatively, the dephasing can be compensated by means of a magnetic gradient pulse, producing an echo signal (gradient echo) in the receiving coils. In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The signal data obtained via the receiving coils corresponds to the spatial frequency domain and are called k-space data. The k-space data usually include multiple lines acquired with different phase encoding. Each line is digitized by collecting a number of samples. A set of k-space data is converted to a MR image by means of Fourier transformation.

In some medical applications, the difference in MR signal intensity from standard MR protocols, i.e. the contrast between different tissues, might not be sufficient to obtain satisfactory clinical information. In this case, contrast enhancing techniques are applied. A particularly promising approach for contrast enhancement and increase of MR detection sensitivity (by orders of magnitude) is the known method based on 'Chemical Exchange Saturation Transfer' (CEST), as initially described by Balaban et al. (see e.g. U.S. Pat. No. 6,962,769 B1) for the application to exogenously administered contrast agents. According to the CEST technique, the image contrast is obtained by altering the intensity of the water proton signal in the presence of a contrast agent or an endogenous molecule with a proton pool resonating at a different frequency than the main water resonance. This is achieved by selectively saturating the nuclear magnetization of the pool of exchangeable protons which resonate at a frequency different from the water proton resonance. Exchangeable protons can be provided by exogenous CEST contrast agents (e.g. DIACEST, PARACEST or LIPOCEST agents), but can also be found in biological tissue (i.e., endogenous amide protons in proteins and peptides, protons in glucose or protons in metabolites like choline or creatinine) A frequency-selective saturation RF pulse that is matched to the MR frequency (chemical shift) of the exchangeable protons is used for this purpose. The saturation of the MR signal of the exchangeable protons is subsequently transferred to the MR signal of nearby water protons within the body of the examined patient by chemical exchange with the water protons, thereby decreasing the water proton MR signal. The selective saturation at the MR frequency of the exchangeable protons thus gives rise to a negative contrast in a water proton based MR image. Amide proton transfer (APT) MR imaging, which is a CEST technique based on endogenous exchangeable protons, allows highly sensitive and specific detection of pathological processes on a molecular level, like increased protein concentrations in malignant tumor tissue. The APT signal is also sensitively reporting on locally altered pH levels—because the exchange rate is pH dependent—which can e.g. be used to characterize acidosis in ischemic stroke. APT/CEST MR imaging has several advantages over conventional MR contrasts. APT/CEST MR imaging allows highly specific detection and differentiation of endogenous contrasts, which is much more sensitive then e.g. spectroscopic MR/NMR techniques. This high sensitivity (SNR efficiency) can be used to obtain molecular contrast information at a resolution comparable to typical MR imaging applications in clinically acceptable examination times. Furthermore, CEST contrasts allow for multiplexing by using a single molecules or a mixture of molecules bearing exchangeable protons that can be addressed separately in a multi-frequency CEST MR examination. This is of particular interest for molecular imaging, where multiple biomarkers may be associated with several unique CEST frequencies. Moreover, the MR contrast in APT/CEST MR imaging can be turned on and off at will by means of the frequency selective preparation RF pulse. Adjustable contrast enhancement is highly advantageous in many applications, for example when the selective uptake of the contrast agent in diseased tissue in the examined body is slow, or for increasing the specificity of detection in areas with highly structured basic MR contrast.

In conventional APT and CEST MR imaging, the effect of the saturation transfer of exchangeable protons to water is identified by an asymmetry analysis of the amplitude of the acquired MR signals as a function of the saturation frequency. This asymmetry analysis is performed with respect to the MR frequency of water protons, which, for convenience, is assigned to a saturation frequency offset of 0 ppm. The measurement of the amplitude of the acquired MR signals as a function of the saturation frequency offset and the asymmetry analysis are inherently very sensitive to any inhomogeneity of the main magnetic field $B_0$. This is because a small shift of the center frequency (e.g. a saturation frequency offset of 0.1 ppm relative to the chemical shift of water) easily causes a variation of more than 10% in the asymmetry data. This variation results in large artifacts in the finally reconstructed APT/CEST MR images.

It has been shown (e.g. Zhou et al., Magnetic Resonance in Medicine, 60, 842-849, 2008) that the $B_0$ inhomogeneity can be corrected in APT/CEST imaging on a voxel-by-voxel basis through re-centering of the asymmetry data on the basis of a separately acquired $B_0$ map. However, an additional $B_0$ mapping scan is required in this known approach. This results in an extended overall imaging time. Several other known methods to correct for $B_0$ inhomogeneity require additional overall scan time to obtain the necessary $B_0$ field inhomogeneity information (e.g. WASSR). Moreover, the separately performed measurement of to obtain the $B_0$ inhomogeneity information is potentially inaccurate or inconsistent, for example because of patient motion, shimming or frequency drift of the used MR device between the field mapping and the actual APT/CEST acquisition. Consequently, the $B_0$ map has to be acquired in close temporal proximity to the APT/CEST scan and potentially needs to be repeated, for example in order to ensure sufficient precision in case of multiple APT/CEST scans within one examination. Thus, the known technique may be severely limited for clinical applications with respect to scan time efficiency and precision.

Another issue in APT and CEST MR imaging is that a robust elimination of signal contributions from fat spins, e.g. by fat saturation RF pulses, is often difficult in the presence of $B_0$ inhomogeneity. However, residual fat signal contributions result in a strongly biased asymmetry of the amplitude of the acquired MR signals as a function of the saturation frequency offset near the chemical shift of fat protons at −3.4 ppm relative to the MR frequency of water protons. This is of particular concern in applications in which MR images of organs with significant fat content are to be acquired, such as the liver or the breast.

The ISMRM 2010 abstract 'CEST-Dixon MRI for sensitive and accurate measurement of amide proton transfer in human 3T' by J. Keupp and H. Eggers discloses a multi-echo T1-weighted gradient echo sequence to acquire APT/CEST MRI. This known approach also employs an iterative Dixon technique to map local field inhomogeneities based on a multi-echo gradient echo approach. This approach provides a $B_0$ field map acquired during the actual APT/CEST acquisition and thus solves some of the above mentioned issues related to additional scan time and workflow/timing for the field mapping as well as the precision of the field characterization,

SUMMARY OF THE INVENTION

From the foregoing it is readily appreciated that there is a need for an improved MR imaging technique. It is consequently an object of the invention to provide a MR imaging method and a MR device which enable high-quality and high contrast-to-noise MR imaging using APT/CEST with efficient and precise intrinsic $B_0$ determination and possible robust elimination of adverse effects due to fat signal contributions.

In accordance with the invention, a method of MR imaging of at least a portion of a body placed in a main magnetic field $B_0$ within the examination volume of a MR device is disclosed. The method of the invention comprises the following steps:
a) subjecting the portion of the body to a saturation RF pulse at a saturation frequency offset;
b) subjecting the portion of the body to an imaging sequence comprising at least one excitation RF pulse and switched magnetic field gradients, whereby MR signals are acquired from the portion of the body as spin echo signals;
c) repeating steps a) and b) two or more times, wherein the saturation frequency offset and/or a echo time shift in the imaging sequence are varied, such that a different combination of saturation frequency offset and echo time shift is applied in two or more of the repetitions;
d) reconstructing a MR image from the acquired MR signals. In accordance with the invention, the portion of the body is subjected to saturation RF pulses each having a saturation frequency offset relative to the MR frequency of water protons. Corresponding to conventional APT/CEST MR imaging, saturation RF pulses are irradiated at different saturation frequency offsets (e.g. near +/−3.5 ppm) around the MR frequency of water protons (0 ppm). After each saturation step, MR signals are acquired by means of a spin echo-type sequence. Preferably a fast spin echo (FSE) or turbo spin echo (TSE) sequence is applied because of the high SNR efficiency provided by this sequence type. Also combined spin echo and gradient echo sequences like the GRASE sequence could be employed. As the compensation of the dephasing is typically less complete in gradient echo base MR pulse sequences due to local variations of the magnetic field (T2*decay), a higher signal-to-noise-ratio (SNR) is achieved in spin echo based MR techniques.

According to the invention, the combinations of saturation frequency offset values and echo time shift values is kept limited. In effect the plane spanned by the offset values and shift values is sparsely sampled by the interation of the imaging sequence at the selected combinations of offset values and shift values. As the number of interations at respective combinations of offset-values and shift-values is limited, the total acquisition time of the APT/CEST acquisition can be limited. In the optimal case, according to the invention, the extra time for $B_0$ field mapping is fully avoided, while the overall acquisition time for a conventional APT/CEST acquisition (requiring $B_0$ information in addition) is not significantly increased. As an example, an efficient 2D APT sampling scheme uses 7 different saturation frequency offsets (e.g. −4, −3.5, −3, +3, +3.5, +4.5 ppm and one image without or with far detuned saturation). The steps of saturation and signal acquisition are repeated, wherein the saturation frequency offset and/or the echo time shift in the imaging sequence are varied. This can be achieved, for example, by varying the timing of the RF refocusing pulse(s), thereby shifting the refocusing of the nuclear magnetization, and/or by varying the timing of the signal acquisition window and associated magnetic field gradients. An essential feature of the invention is that different and selected combinations of saturation frequency offset and echo time shift are applied in different repetitions. A subset of specific combinations are selected which can be efficiently used to obtain APT/CEST images with intrinsic magnetic field homogeneity correction. Finally, MR images is reconstructed from the acquired MR signals, which may be quantitative APT/CEST images or APT/CEST weighted images.

The known technique is strictly limited to gradient echo type MR sequences, which excludes the use of highly contrast-to-noise ratio efficient spin echo type acquisitions. A spin echo based Dixon technique is not scan time efficient for APT/CEST, because it requires multiple full image acquisitions with different echo shifts for one or even for all saturation frequency offsets. Thus, in a conventional spin echo Dixon approach, the APT/CEST overall acquisition time would be significantly increased to obtain the field inhomogeneity information, similar to the techniques using separate $B_0$ mapping. For a conventional 3-point spin echo Dixon reconstruction of the field inhomogeneity (to provide one $B_0$ map, no fat separation across the z-spectrum), at least one of the offsets has to be fully acquired 3 times. This would require at least two additional full images and a scan time increase of 30%. Separate $B_0$ mapping (e.g. dual-echo gradient echo based) needs about the same or even more extra scan time. $B_0$ map information needs to be acquired with sufficient SNR, thus, typically about 1 minute of acquisition time is required 2D (and more for 3D).

Since MR signals are acquired as spin echo signals at different echo time shifts, the spatial variation of $B_0$ within the portion of the body can be determined from the acquired MR signals by means of a multi-point Dixon technique. According to the per se known Dixon technique, the spectral difference between fat and water spins is made use of for the purpose of separating MR signals emanating from water containing tissue and MR signals emanating from fat tissue. In spin echo Dixon imaging, multiple acquisitions of k-space are repeated with different echo time shifts. The simplest Dixon technique, a two-point Dixon technique, acquires two complete k-space data sets, wherein the fat magnetization in the second acquisition shows a phase difference (e.g. 180°=out phase) relative to the water magnetization, and a different phase difference (e.g. 0°=in phase) in the first acquisition. In the case of out phase and in phase images, separate and distinct water and fat images can be obtained by simple addition or subtraction of the complex MR signal data. In general, a $B_0$ field map, a water image and a fat image are obtained by means of a Dixon technique, which may include an iterative reconstruction approach. Hence, also the spatial variation of $B_0$ within the portion of the body can be determined from the MR signals acquired in accordance with the invention by means of the single- or multi-point spin echo Dixon technique. The method of the invention thus permits the application of Dixon methods for both $B_0$ mapping as well as water/fat separation simultaneously in the context of spin echo MRI. The method of the invention integrates spin echo Dixon methods into APT/CEST MR imaging in an efficient manner.

The reconstruction of the MR image according to the invention may include deriving the spatial distribution of amide protons within the portion of the body from an asymmetry analysis or other z-spectral analysis technique based on the amplitude of the acquired MR signals as a function of the saturation frequency offset, wherein the z-spectral analysis involves a saturation frequency offset correction based on the spatial variation of $B_0$ determined by means of the applied Dixon method. The approach of the invention thus enables correcting for $B_0$ inhomogeneity in APT/CEST MR imaging by integration of spin echo Dixon methods.

Moreover, the reconstruction of the MR image according to the invention may include deriving the spatial pH distribution within the portion of the body from the asymmetry analysis or other z-spectral analysis technique on the basis of the amplitude of the acquired MR signals as a function of the saturation frequency. Again, the z-spectral analysis may involve a saturation frequency offset correction based on the determined spatial variation of $B_0$.

According to the invention, the saturation RF pulses are applied in different repetitions of steps a) and b) at positive and negative saturation frequency offsets around the resonance frequency of water protons. As in conventional APT/CEST MR imaging, different saturation frequency offsets (e.g. near +/−3.5 ppm) around the MR frequency of water protons are applied. Steps a) and b) may be repeated two or more times with the same saturation frequency offset but simultaneously applying a different echo time shift in each repetition. This could by implemented such that the acquisition with any saturation frequency offset is repeated two or three times, each with a different echo time shift. Alternatively, steps a) and b) are repeated two or more times with a different saturation frequency offset and with a different echo time shift in two or more of the repetitions. This means that both the saturation frequency offset and the echo time shift are simultaneously varied in the repetitions. The latter scheme is preferably applied for saturation frequency offsets that are positive with respect to the resonance frequency of water protons. For positive saturation frequency offsets, the amplitude of the MR signals of water protons can be expected to vary only slightly between the individual repetitions of steps a) and b) due to different extents of direct saturation of water protons and due to the relevant saturation transfer effects e.g. near +3.5 ppm (APT), while the MR signal amplitude of fat protons is expected to stay constant. In order to assure the condition of minor amplitude variations of the order of <10% among the repetitions with different frequency offsets and echo shifts, the saturation frequency offsets of at least two repetitions need to be placed in close frequency proximity (e.g. 0.5 ppm apart for APT). In contrast, the contribution of fat protons to the overall MR signal amplitude may be modulated substantially at negative saturation frequency offsets in the proximity of the saturation frequency corresponding to the chemical shift-induced frequency of fat protons (−3.4 ppm). Therefore, the spin echo Dixon type $B_0$ mapping, according to the invention, is preferably based on the MR signal acquisitions with positive saturation frequency offsets. The obtained $B_0$ map can subsequently be employed for water-fat separation at all saturation frequency offsets, e.g. by means of a single-point or multi-point Dixon technique.

The method of the invention described thus far can be carried out by means of a MR device including at least one main magnet coil for generating a uniform steady magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstruction of a MR image from the received MR signals. The method of the invention is preferably implemented by a corresponding programming of the control unit and/or the reconstruction unit of the MR device.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
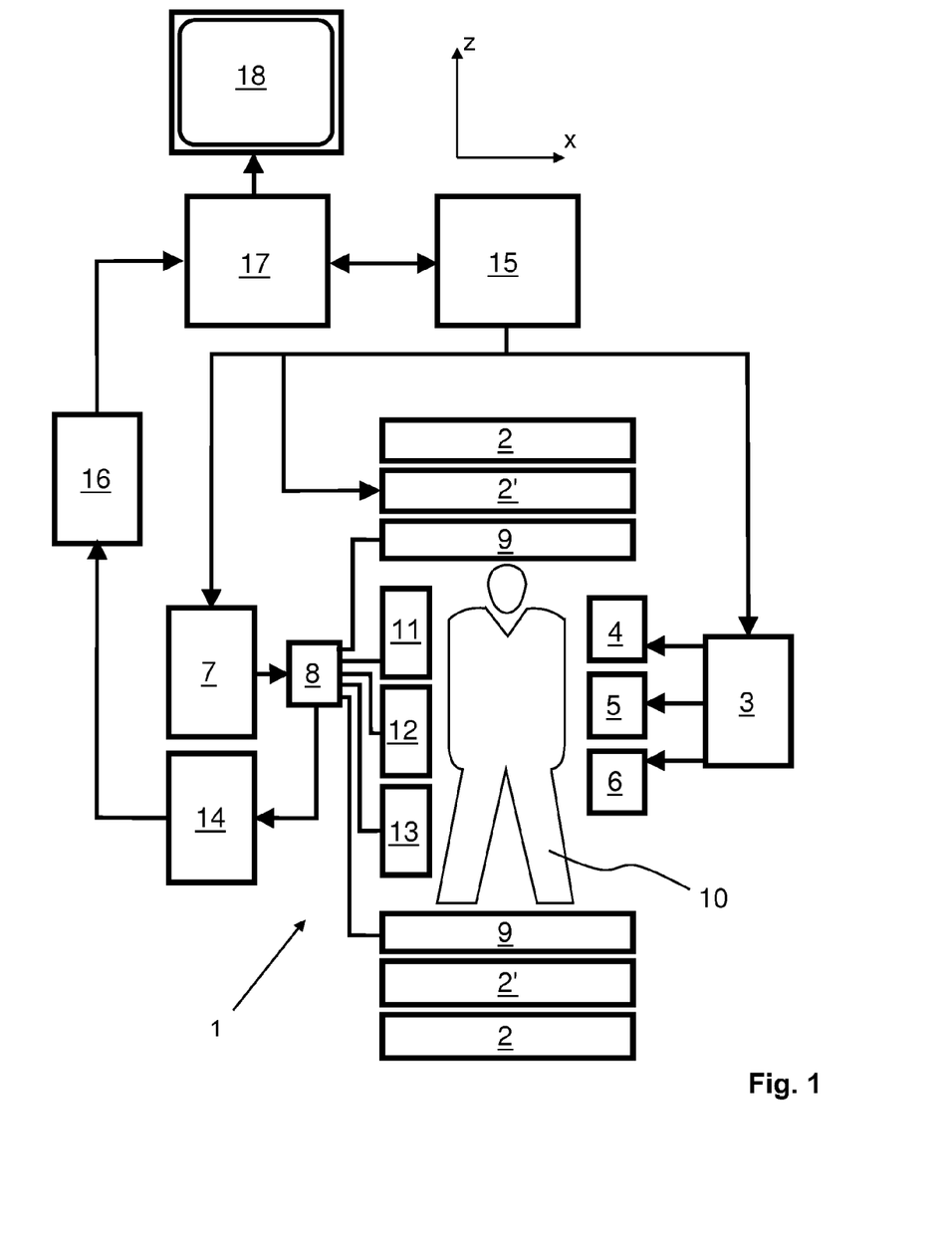
FIG. 1 shows a MR device according to the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 or to a set of local array RF coils 11, 12, 13, to transmit RF pulses into the examination volume. A typical MR imaging sequence is composed of a packet of RF pulse segments which, together with any applied magnetic field gradients, achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions.

The resultant MR signals are picked up by the body RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the shimming coils 2' as well as the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in the acquisition of raw image data.

Ultimately, the digital raw image data are reconstructed into an image representation by a reconstruction processor 17 which applies a Fourier transform or other appropriate reconstruction algorithms, such as SENSE or GRAPPA. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

Figure 2:
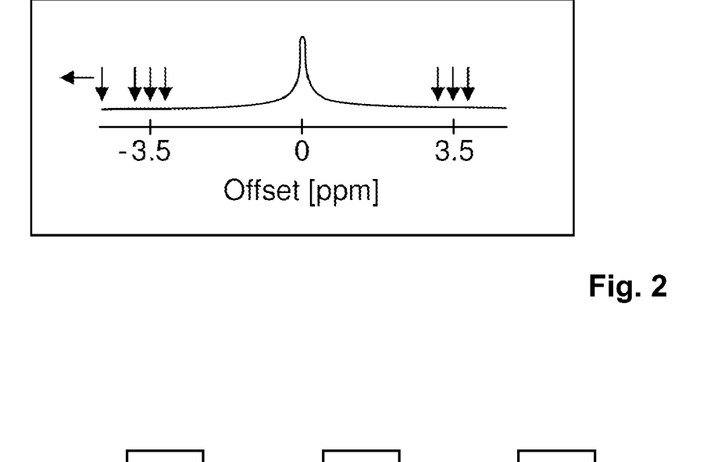
FIG. 2 shows a diagram illustrating the scheme of saturation frequency offsets used for APT MR imaging according to the invention.

In accordance with the invention, the portion of the body 10 is subjected to saturation RF pulses at different saturation frequency offsets prior to acquisition of MR signals by means of a spin echo sequence, which is preferably a fast spin echo (FSE) or turbo spin echo (TSE) sequence or a related pulse sequence like GRASE (a combined spin echo and gradient echo sequence). The saturation RF pulses are irradiated via the body RF coil 9 and/or via the array RF coils 11, 12, 13, wherein the saturation frequency offset relative to the MR frequency of water protons is set by appropriate control of the transmitter 7 via the host computer 15. As shown in FIG. 2, different saturation frequency offsets are applied around +/−3.5 ppm around the MR frequency of water protons (0 ppm). The different saturation frequency offsets are indicated by black arrows in FIG. 2. A further reference acquisition may be performed "off-resonant", i.e. with a very large frequency offset which leaves the MR signal amplitude of water protons unaffected or with the RF saturation power switched off, which is useful for signal normalization (quantification of the z-spectral asymmetry). This is indicated by the leftmost black arrow in FIG. 2.

According to the invention, MR signal acquisition steps are repeated several times, wherein the saturation frequency offset and the echo time shifts in the spin echo sequence are varied, such that a different combination of saturation frequency offset and echo time shift is applied in two or more of the repetitions. Finally, an APT/CEST MR image is reconstructed from the acquired MR signals. This means that the reconstruction of the MR image includes deriving the spatial distribution of amide protons within the portion of the body 10 from an asymmetry analysis or a similar z-spectral analysis technique base on the amplitude of the acquired MR signals as a function of the saturation frequency offset. This z-spectral analysis, which is conventionally applied in APT/CEST MR imaging, is very sensitive to any inhomogeneity of the main magnetic field $B_0$. This is taken into account by the method of the invention by determination of the spatial variation of $B_0$ from the acquired MR signals by means of a multi-point Dixon technique. The determined spatial variation of $B_0$ is then used for a corresponding saturation frequency offset correction in the asymmetry analysis or other z-spectral analysis technique.

For a determination of the spatial variation of $B_0$, two specific strategies may be applied in accordance with the invention. These strategies are illustrated in the diagrams of FIGS. 3 and 4.

Figure 3:
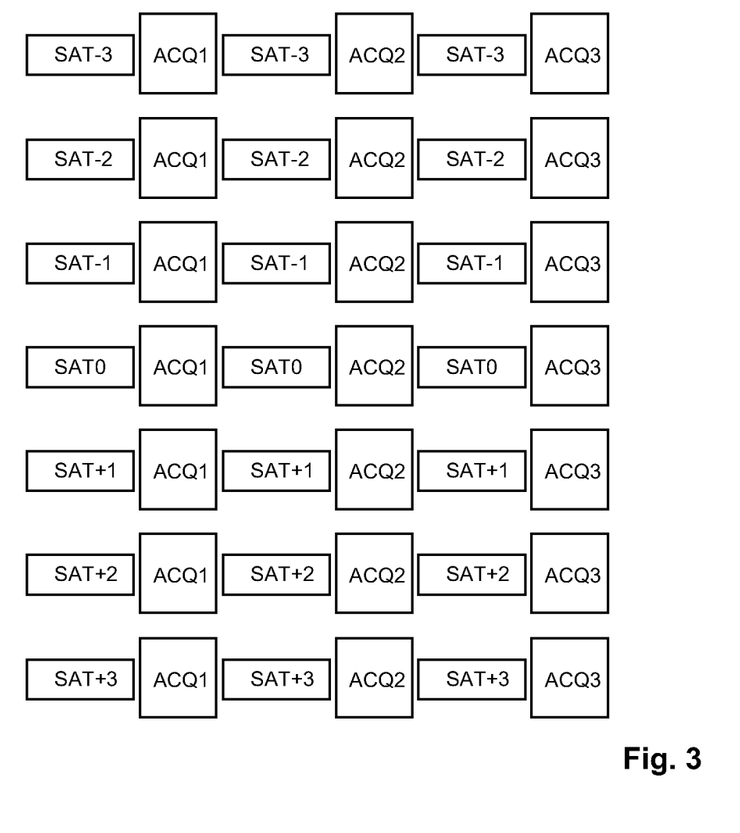
FIG. 3 shows a diagram illustrating a first embodiment of the APT acquisition scheme according to the invention.
Figure 4:
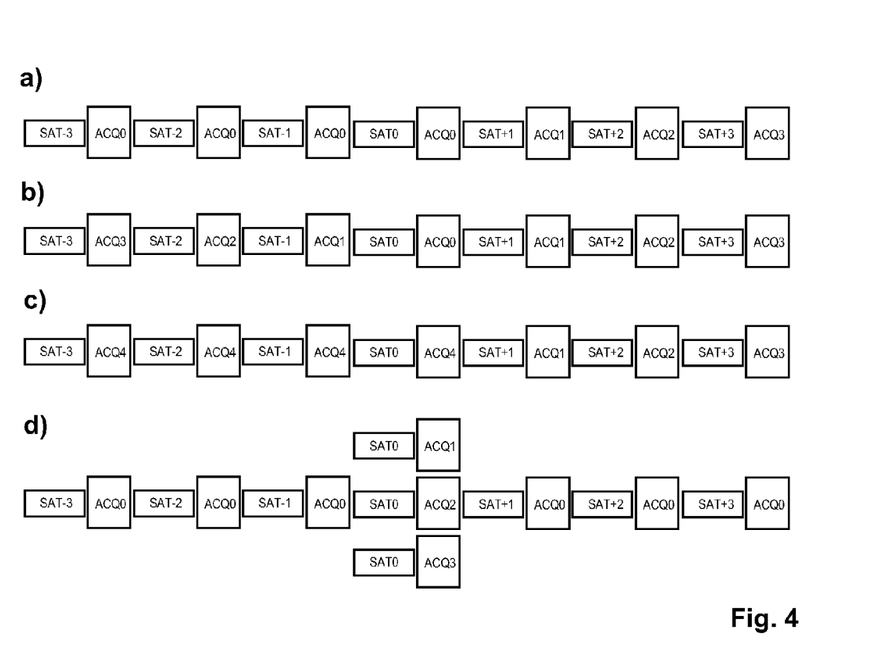
FIG. 4 shows a diagram illustrating a second embodiment of the APT acquisition scheme according to the invention.

The saturation steps are indicated in FIGS. 3 and 4 by SAT−3, SAT−2, SAT−1, SAT0, SAT+1, SAT+2 and SAT+3. Therein, SAT−1, SAT−2 and SAT−3 correspond to negative saturation frequency offsets, while SAT+1, SAT+2 and SAT+3 correspond to positive saturation frequency offsets. SAT0 corresponds to a reference measurement, in which an off-resonant frequency offset is applied, as mentioned above. ACQ1, ACQ2, ACQ3 and ACQ4 indicate MR signal acquisition steps using different echo time shifts ($TE_1$, $TE_2$, $TE_3$, $TE_4$), respectively.

In the embodiment shown in FIG. 3, an acquisition with any saturation frequency offset SAT−3, SAT−2, SAT−1, SAT0, SAT+1, SAT+2 and SAT+3 is repeated three times, each with a different echo time shift, indicated by ACQ1, ACQ2, and ACQ3. This results in an overall number of 21 repetitions. $B_0$ mapping is preferably performed separately for each saturation frequency offset.

In the further embodiments shown FIG. 4, the acquisitions with different saturation frequency offsets SAT−3, SAT−2, SAT−1, SAT+1, SAT+2, SAT+3 are performed only once, but with different echo time shifts, indicated by ACQ1, ACQ2, ACQ3 and ACQ4 (echo times $TE_1$, $TE_2$, $TE_3$, $TE_4$). ACQ0 indicates an acquisition without echo time shift (echo time $TE_0$). A multi-point (iterative) Dixon technique is applied to derive the $B_0$ map from these acquisitions combining the data from different saturation frequency offsets, according to the invention. In FIG. 4a three different echo time shifts (indicated by ACQ1, ACQ2, ACQ3) are applied with the saturation frequency offsets SAT+1, SAT+2 and SAT+3. The $B_0$ map is derived from these acquisitions. No echo time shift is applied in the acquisitions with SAT−3, SAT−2, SAT−1 and SAT0. The $B_0$ map is applied for correction in these acquisitions. In FIG. 4b the different echo time shifts are also applied with SAT−3, SAT−2, SAT−1. No echo time shift is applied for SAT0. In FIG. 4c three different echo time shifts (that are well-suited for 3-point Dixon $B_0$ mapping) are applied with saturation frequency offsets SAT+1, SAT+2, SAT+3, while a single echo time shift that is well-suited for water/fat separation (indicated by ACQ4) is applied with saturation frequency offsets SAT0, SAT−1, SAT−2 and SAT−3. In FIG. 4d no echo time shift is applied for SAT−3, SAT−2, SAT−1 and SAT+1, SAT+2, SAT+3, while three different echo time shifts are applied with SAT−0 (for $B_0$ mapping).

For positive saturation frequency offsets which are placed in close spectral proximity of the chemical shift of the exchangeable proton pool in question (e.g. +3.5 ppm for APT), the MR signal amplitude of water protons is expected to vary slightly (<10%) between the individual acquisitions due to different extents of direct saturation of water protons and due to the relevant saturation transfer effects, as mentioned above. The resulting signal variation may be addressed in different ways for the purpose of $B_0$ mapping. One option is to simply ignore this small signal variation. This option can be used in practice, in particular in combination with specifically positioned saturation frequency offsets, but it may potentially result in a somewhat reduced precision of the determined $B_0$ map. Another option is to minimize the influence of the signal variations by choosing appropriate echo time shifts, where the Dixon-based $B_0$ determination is most robust against signal variations. A further option is to apply an appropriate mathematical model of the acquired composite complex MR signals and to derive the $B_0$ from the resulting model parameters. Different strategies for MR signal modeling in Dixon imaging exist, which can be applied in accordance with the invention, and which are per se known in the art.

In an embodiment of the invention, the composite complex signal S acquired with SAT+1, SAT+2, SAT+3 may be modeled by:

$$S_{+1} = (W_1 + c_1 F) P \Delta P^*$$

$$S_{+2} = (W_2 + c_2 F) P$$

$$S_{+3} = (W_3 + c_3 F) P \Delta P$$

or, by using a linear approximation, as:

$$S_{+1} = (W - \Delta W + c_1 F) P \Delta P^*$$

$$S_{+2} = (W + c_2 F) P$$

$$S_{+3} = (W + \Delta W + c_3 F) P \Delta P,$$

wherein W denotes the water signal contribution, F denotes the fat signal contribution, P and $\Delta P$ denote phase errors, and c denotes coefficients that describe the amplitude and phase of a unit fat signal at the respective echo time shift. W, F, P, and $\Delta P$ are considered as unknowns, while S and c are considered as knowns. In the first case (without approximation), the number of knowns (real and imaginary components of S) and the number of unknowns (real $W_1$-$W_3$, real F, phase of P and $\Delta P$) are both equal to six. In the second case (with approximation), the number of knowns exceeds the number of unknowns by one. The acquisition with saturation frequency offset SAT0 may be included as fourth equation, again with a different W and the same F. $B_0$ can be derive on a voxel-by-voxel basis from the resulting model parameters.

The spatial variation of $B_0$ can be assumed not to change between the individual MR signal acquisition steps to acquire the different saturation frequency offsets for APT/CEST MRI. Accordingly, once the spatial variation of $B_0$ has been determined in the afore-described manner, the obtained $B_0$ map can be used for suppression of signal contributions from fat spins. A Dixon method can be applied to perform a water/fat separation after demodulation of $B_0$-induced phase errors. The echo time values can be optimized to maximize the signal-to-noise ratio in the resulting water MR images, for instance by choosing echo time shifts at which signal contributions from water and fat spins are in quadrature, i.e. 90° out of phase. If other echo time values are preferred for $B_0$ mapping than are favorable for Dixon water/fat separation, some acquisitions with appropriate saturation frequency offsets may be repeated with correspondingly chosen echo time values.

For positive saturation frequency offsets, one of the schemes illustrated in FIG. 4 for obtaining the $B_0$ map can also be employed to suppress signal contributions from fat spins. For the acquisitions with negative saturation frequency offsets near the chemical shift of fat protons, the extent of saturation of fat protons imposed by the saturation RF pulses can be modeled on the basis of an appropriate mathematical model, taking the RF pulse parameters (for example shape, bandwidth) and the spectrum of the fat protons (for example number of peaks, resonance frequencies, resonance areas, line widths) into account.

In an exemplary embodiment, the composite signal S acquired with SAT-1, SAT-2, SAT-3 may be modeled as:

$$S_{-1} = (W_1 + c_1 d_1 F) P \Delta P^*$$

$$S_{-2} = (W_2 + c_2 d_2 F) P$$

$$S_{--3} = (W_3 + c_3 d_3 F) P \Delta P$$

or, using a linear approximation, as:

$$S_{-1} = (W - \Delta W + c_1 d_1 F) P \Delta P^*$$

$$S_{-2} = (W + c_2 d_2 F) P$$

$$S_{-3} = (W + \Delta W + c_3 d_3 F) P \Delta P,$$

wherein d denotes coefficients that describe the relative extent of fat suppression. For the acquisitions with both, positive and negative saturation frequency offsets, F may be considered as unknown, or F may be considered as known from the water/fat separation in the acquisition with off-resonant saturation SAT0.

After water/fat separation, an APT/CEST MR image at the desired saturation offset frequency (e.g. +3.5 ppm for APT) can be reconstructed by means of the above-mentioned asymmetry analysis or other z-spectral analysis technique based on the voxel-wise amplitude of the water MR images as a function of the saturation frequency offset. Therein, the asymmetry/z-spectral analysis involves a saturation frequency offset correction based on the determined spatial variation of $B_0$, e.g. by means of a voxel-by-voxel Lagrange interpolation of the images taken at different saturation frequency offsets.

The invention claimed is:

1. A method of MR imaging of at least a portion of a body placed in a main magnetic field $B_0$ within the examination volume of a MR device, the method comprising the following steps:
   a) subjecting the portion of the body to a saturation RF pulse at a saturation frequency offset respective to the resonance frequency of water protons;
   b) subjecting the portion of the body to an imaging sequence comprising excitation and refocusing RF pulses and switched magnetic field gradients, whereby MR signals are acquired from the portion of the body as spin echo signals;
   c) repeating steps a) and b) two or more times, wherein at least one of the saturation frequency offset and an echo time shift in the imaging sequence are varied, such that a different combination of saturation frequency offset and echo time shift is applied in two or more of the repetitions;
   d) reconstructing a MR image as $B_0$ field homogeneity corrected amide proton transfer (APT)/Chemical Exchange Saturation Transfer (CEST) images from the acquired MR signals;
   wherein the reconstructing includes determining a spatial variation of $B_0$ within the portion of the body from the acquired MR signals using a multi-point Dixon technique based on MR signal acquisitions with different saturation frequency offsets and different echo time shifts.

2. The method of claim 1 wherein
   the repeating of steps a) and b) includes repeating with a number of offset-values for the saturation frequency offset and a number of shift-values for the echo-time shift are selected and
   for each of the respective different selected offset-values a different shift value for the echo time shift is applied in the imaging sequence.

3. The method of claim 2, wherein the applied offset-values and the applied shift values effect a sparse sampling of a plane spanned by offset values and shift values.

4. The method of claim 1, wherein the spatial variation of $B_0$ within the portion of the body is determined from the acquired MR signals using the multi-point Dixon technique based on the MR signal acquisitions with the different saturation frequency offsets that are positive with respect to the resonance frequency of water protons.

5. The method of claim 1, wherein the reconstruction of the MR image includes deriving a spatial distribution of amide protons within the portion of the body from an asymmetry analysis of the amplitude of the acquired MR signals as a function of the saturation frequency offset respective to the resonance frequency of water protons, which asymmetry analysis involves a saturation frequency offset correction based on the determined spatial variation of $B_0$.

6. The method of claim 5, wherein the reconstruction of the MR image includes deriving a spatial pH distribution within the portion of the body from an asymmetry analysis of the amplitude of the acquired MR signals as a function of the saturation frequency offset respective to the resonance frequency of water protons, which asymmetry analysis involves a saturation frequency offset correction based on the determined spatial variation of $B_0$.

7. The method of claim 1, wherein saturation RF pulses are applied in different repetitions of steps a) and b) at positive and negative saturation frequency offsets around the resonance frequency of water protons.

8. The method of claim 1, wherein steps a) and b) are repeated two or more times with the same saturation frequency offset and with a different echo time shift in two or more of the repetitions.

9. The method of claim 1, wherein steps a) and b) are repeated two or more times with a different saturation frequency offset and with a different echo time shift in two or more of the repetitions.

10. The method of claim 1, wherein the repeating of steps a) and b) generates exactly one combination of saturation frequency offset and echo time shift for each saturation frequency offset.

11. The method of claim 1, wherein the determining of the spatial variation of $B_0$ within the portion of the body produces a single $B_0$ map which is used in the $B_0$ field homogeneity correction of all of the $B_0$ field homogeneity corrected APT/CEST images.

12. A magnetic resonance (MR) device comprising:
   at least one main magnet coil for generating a uniform, steady magnetic field within an examination volume;
   a number of gradient coils for generating switched magnetic field gradients in different spatial directions within the examination volume;
   at least one RF coil for generating RF pulses within the examination volume and/or for receiving MR signals from a body of a patient positioned in the examination volume; and
   a computer programmed to control the temporal succession of RF pulses generated by the at least one RF coil and switched magnetic field gradients generated by the gradient coils and to reconstruct an MR image from the received MR signals by performing the following steps:
   a) subjecting the portion of the body to a saturation RF pulse generated by the at least one RF coil at a saturation frequency offset with respect to the resonance frequency of water protons;
   b) subjecting the portion of the body to an imaging sequence comprising excitation and refocusing RF pulses generated by the at least one RF coil and switched magnetic field gradients generated by the gradient coils, whereby MR signals are acquired from the portion of the body as spin echo signals;
   c) repeating steps a) and b) two or more times, wherein at least one of the saturation frequency offset and an echo time shift in the imaging sequence are varied, such that a different combination of saturation frequency offset and echo time shift is applied in two or more of the repetitions;
   d) reconstructing an MR image as $B_0$ field homogeneity corrected amide proton transfer (APT)/Chemical Exchange Saturation Transfer (CEST) images from the acquired MR signals;
   wherein the reconstructing includes determining a spatial variation of $B_0$ within the portion of the body from the acquired MR signals using a Dixon technique based on MR signal acquisitions with different saturation frequency offsets and different echo time shifts to produce a single $B_0$ map which is used in the $B_0$ field homogeneity correction of all of the $B_0$ field homogeneity corrected APT/CEST images.

13. A non-transitory data carrier storing a computer program to be run on a magnetic resonance (MR) device, which computer program comprises instructions for causing the MR device to perform a method including:
   a) generating a saturation RF pulse at a saturation frequency offset with respect to the resonance frequency of water protons;
   b) generating an imaging sequence comprising excitation and refocusing RF pulses and switched magnetic field gradients, whereby MR signals are acquired from the portion of the body as spin echo signals;
   c) repeating steps a) and b) two or more times, wherein at least one of the saturation frequency offset and an echo time shift in the imaging sequence are varied, such that a different combination of saturation frequency offset and echo time shift is applied in each of the two or more of the repetitions and the repetitions generate exactly one combination of saturation frequency offset and echo time shift for each saturation frequency offset;
   d) reconstructing an MR image as $B_0$ field homogeneity corrected amide proton transfer (APT)/Chemical Exchange Saturation Transfer (CEST) images from the acquired MR signals;
   wherein the reconstructing includes determining a spatial variation of $B_0$ within the portion of the body from the acquired MR signals using a Dixon technique based on MR signal acquisitions with different saturation frequency offsets and different echo time shifts.

\* \* \* \* \*